United States Patent [19]
Restaino

[11] Patent Number: 6,087,156
[45] Date of Patent: Jul. 11, 2000

[54] METHOD FOR ISOLATION AND IDENTIFICATION OF *ESCHERICHIA COLI* 0157:H7 AND PLATING MEDIA FOR SAID PROCESS

[75] Inventor: Lawrence Restaino, Elburn, Ill.

[73] Assignee: R&F Laboratories, Inc., West Chicago, Ill.

[21] Appl. No.: 09/178,019

[22] Filed: Oct. 23, 1998

Related U.S. Application Data

[63] Continuation of application No. 08/714,690, Sep. 16, 1996, abandoned.

[30] Foreign Application Priority Data

Sep. 16, 1997 [WO] WIPO ............... PCT/US07/17176

[51] Int. Cl.[7] ................................................ C12M 1/00
[52] U.S. Cl. ............... 435/287.9; 435/7.37; 435/7.21; 435/34; 435/39; 435/40; 435/395; 435/404
[58] Field of Search ..................... 435/7.21, 7.37, 435/287.9, 34, 39, 40, 395, 404

[56] References Cited

U.S. PATENT DOCUMENTS

| | | | |
|---|---|---|---|
| 5,354,661 | 10/1994 | Doyle et al. | 435/7.37 |
| 5,733,736 | 3/1998 | Wun | 435/7.21 |
| 5,750,363 | 5/1998 | Ollar et al. | 435/29 |
| 5,854,013 | 12/1998 | Ollar et al. | 435/34 |
| 5,962,306 | 10/1999 | Ollar et al. | 435/287.9 |

FOREIGN PATENT DOCUMENTS 9202820  2/1992  WIPO .

*Primary Examiner*—Christopher L. Chin
*Assistant Examiner*—Ginny Allen Portner
*Attorney, Agent, or Firm*—Marshall A. Burmeister

[57] ABSTRACT

A solid plating medium for the presumptive detection of *Escherichia coli* 0157:H7 which comprises (1) an ingredient which promotes growth of *Escherichia coli* cells under incubation, (2) an ingredient which inhibits growth of gram positive microorganisms under incubation, (3) an ingredient that inhibits growth of Proteus sp. under incubation, (4) an ingredient which inhibits the growth of strains of *Escherichia coli* other than *Escherichia coli* 0157:H7 under incubation, (5) a carbohydrate medium that under incubation is not fermented by *Escherichia coli* 0157:H7 but which is fermented by other microorganisms including other strains of *Escherichia coli,* (6) a pH indicator dye which changes the plating media to a first color when the pH of the medium changes, (7) a chromogenic beta-galactosidase substrate that produces precipitate of a second color responsive to beta-galactosidase, the first color contrasting with the second color and the first and second colors blending to produce a third color which contrasts with the first and second colors, and (8) a mass of agar sufficient to solidify the mixture. Also, the method of detecting the presence of *Escherichia coli* 0157:H7 comprising inoculating the solid plating medium set forth above with a test sample containing *Escherichia coli* including *Escherichia coli* 0157:H7, then incubating said plating medium for a period sufficient to obtain colonies of microorganisms and generating one or more of the colors produced by the plating medium, and then examining the surface of the medium for the presence of colonies of the second color.

19 Claims, No Drawings

METHOD FOR ISOLATION AND IDENTIFICATION OF *ESCHERICHIA COLI* 0157:H7 AND PLATING MEDIA FOR SAID PROCESS

This application is a continuation of application Ser. No. 08/714,690, filed Sep. 16, 1996 now abandoned. The present invention relates to a process for isolating *Escherichia coli* 0157:H7 from other strains of *Escherichia coli* and other microorganisms, and to a solid plating media suitable for use in that process.

BACKGROUND OF THE INVENTION

*Escherichia coli* 0157:H7 has been recognized as an important human pathogen. Studies have shown that it is principally transmitted through food, *Escherichia coli* 0157:H7: *Epidemiology, Pathogenesis, and Methods for Detection in Food,* Nisha V. Padhye and Michael P. Doyle—*Journal of Food Protection,* Vol. 55, No. 7, Pages 555–565 (July 1992). There is thus a need for a rapid diagnostic test for the presence of *Escherichia coli* 0157:H7 in food in order to prevent the spread of *Escherichia coli* 0157:H7 through the food supply.

Pradhye and Doyle, supra, survey methods of detection of *Escherichia coli* 0157:H7. A stable characteristic of *Escherichia coli* 0157:H7 is that it will not ferment sorbitol within 24 hours whereas other strains of *Escherichia coli* will produce fermentation in sorbitol under incubation temperatures within 24 hours, and this characteristic has been used in processes for the isolation of *Escherichia coli* 0157:H7 from other enterics. Since there are microorganisms other than *Escherichia coli* 0157:H7 that do not ferment sorbitol, including some strains of *Escherichia coli,* this characteristic is not sufficiently specific to serve as an identifying test for *Escherichia coli* 0157:H7.

Anita J. Okrend, Bonnie E. Rose and Charles P. Lattuada describe an improved plating medium in *Use of 5-Bromo-4-Chloro-3-Indoxyl-Beta-D-Glucuronide in MacConkey Sorbitol Agar in the Isolation of Escherichia coli 0157:H7 from Ground Beef, Journal of Food Protection,* Vol. 53, No.11, Pages 941–943 (November 1990). This article describes a plating medium in which 5-bromo-4-chloro-3-indoxyl-beta-D-glucuronide acid cyclohexylammonium salt was dissolved in ethanol and the solution added to MacConkey Sorbitol Agar. Since approximately 97% of all *Escherichia coli* are beta-glucuronidase positive, but *Escherichia coli* 0157:H7 is beta-glucuronidase negative, this medium responds to the presence of *Escherichia coli* 0157:H7 by isolating white colonies rather than isolating blue colonies resulting from beta-glucuronidase positive microorganisms.

The process of isolating and detecting the presence of *Escherichia coli* 0157:H7 in a test sample by means of the processes described above, requires inoculation of the plating medium with the test sample, incubating the inoculated plating medium for a period of time, usually over night, and examining the surface of the plating medium to locate colonies of microorganisms in the incubated plating medium. Identification of *Escherichia coli* 0157:H7 is determined by the shape of the colony, size of the colony and color of the colony in the plating medium.

The color of the colony in the plating medium is a characteristic of the particular medium. U.S. Pat. No. 5,464,755 of Barry Bochner entitled *Microbiological Medium and Method of Assay; for Bacteria* describes a plating medium adapted to produce colonies in three different colors. The examination of incubated plating media under a microscope is an exacting and time consuming task, and in the plating methods of the prior art, a positive response results in a presumptive identification of *Escherichia coli* 0157:H7 which must be verified by other testing methods. In short, an identification of *Escherichia coli* 0157:H7 cannot be made by prior art methods in less than about one day and at substantial expense due to the labor required to analyze the plating medium and the cost of the plating materials.

In an article published in the *Journal of Microbiology*—Volume 39 (1993) at pages 133–158, by P. M. Zadik, P. A. Chapman and C. A. Siddons, entitled *Use of Tellurite for the Selection of Verocytotoxigenic Escherichia coli 0157:H7,* experiments are described in which plating media containing mixtures of MacConkey sorbitol and potassium tellurite are subjected to mixed cultures of microorganisms. It was found that such plating media can be effective to reduce the growth of other strains of *Escherichia coli* than *Escherichia coli* 0157:H7 without materially affecting the growth of *Escherichia coli* 0157:H7. Further, such plating media were found to suppress the growth of other important enteric microorganisms, excepting Shigella.

STATEMENT OF INVENTION

It is an object of the present invention to provide a method of isolating and presumptively identifying *Escherichia coli* 0157:H7 which utilizes solid plating media and is more reliable than plating media methods known to the art, that is, makes a positive presumptive identification of *Escherichia coli* 0157:H7 and reduces the percentage of false positive determinations from that of prior art plating methods.

It is a further object of the present invention to provide a method of isolating and presumptively identifying *Escherichia coli* 0157:H7 which utilizes a solid plating medium and achieves its results in a significantly shorter time than processes of the prior art.

It is a further object of the present invention to provide a method of isolating and presumptively identifying *Escherichia coli* 0157:H7 which utilizes a solid plating medium and achieves its results at a significantly lower cost than processes of the prior art.

It is also an object of the present invention to provide plating media adapted for use in the methods described above.

The present invention comprises a solid plating medium which utilizes three mechanisms to produce an indication of the presence of *Escherichia coli* 0157:H7 in a test sample. First, the plating medium contains one or more carbohydrates which are not fermented by *Escherichia coli* 0157:H7 but may be fermented by other microorganisms including other strains of *Escherichia coli*. If a microorganism is present which ferments the carbohydrate, the medium is selected to change to a first color and indicates the presence of a microorganism other than *Escherichia coli* 0157:H7. Second, the plating medium contains a chromogen responsive to the presence of beta-galactosidase, and third, the plating medium contains ingredients for restricting the growth of microorganisms other than *Escherichia coli* 0157:H7.

More specifically, a solid plating medium for the presumptive identification of *Escherichia coli* 0157:H7 according to the present invention comprises: (1) at least one ingredient for differentiating *Escherichia coli* cells under incubation which is not fermented by *Escherichia coli* 0157:H7 but is fermented by other microorganisms including other strains of *Escherichia coli,* and if fermented results in a change in the pH of the medium; (2) a pH indicator dye which changes to a first color when the pH of the medium changes, (3) an ingredient for inhibiting the growth of gram positive microorganisms under incubation; (4) an ingredient for inhibiting the growth of Proteus sp. under incubation; (5) an ingredient for inhibiting the growth of strains of *Escherichia coli* other than *Escherichia coli* 0157:H7 under incubation; and (6) a chromogenic substrate that upon reacting to beta-galactosidase forms a second color that can contrast with the first color and combine with the first color to form a third color which contrasts with the first and second colors, however *Escherichia coli* 0157:H7 retains the second color.

The method of presumptive identification of *Escherichia coli* 0157:H7 according to the present invention comprises inoculating a mass of the plating medium described above with the sample under test, thereafter incubating the mass of inoculated plating medium at a temperature between 30 degrees and 40 degrees Celsius for a sufficient period to produce microorganism colonies in the mass of plating medium, and thereafter examining the surface of the mass of plating medium for colonies of the second color. Emergence of the first or a third color which is a blend of the first and second colors indicates the presence of microorganisms other than *Escherichia coli* 0157:H7.

The invention will be more readily understood from the following detailed description of the invention, which contains no drawing.

DETAILED DESCRIPTION OF THE INVENTION

The inventors' preferred detection system for *Escherichia coli* 0157:H7 utilizes solid plating medium containing sorbitol, adonitol, salicin, inositol, indoxyl-beta-D-galactopyranoside and tellurite. Growth of microorganisms in this medium, specifically including *Escherichia coli* 0157:H7, can result in production of beta-galactosidase, which reacts with indoxyl-beta-D-galactopyranoside to produce an insoluble precipitate with a blue color. Hence, the presence of colonies of microorganisms which produce beta-galactosidase in the medium and do not produce acids from the carbohydrates are blue and clearly visible and defined.

The presence of tellurite in the medium suppresses the growth of most microorganisms other than *Escherichia coli* 0157:H7, and a few others which are suppressed by other means to be described hereinafter. Hence, the observance of blue with black precipitate colonies on the surface of the plating medium is a direct indication of *Escherichia coli* 0157:H7 and a presumptive identification.

While *Escherichia coli* 0157:H7 is sorbitol, adonitol, salicin and inositol negative, >99.0% of *Escherichia coli*, and most other enteric microorganisms, are positive for these carbohydrates. Microbial fermenting of sorbitol, adonitol, salicin and inositol changes the pH of the medium, thus producing colonies influenced by the indicator dye, i.e. yellow in the following examples. Hence, the presence of a yellow colony on the surface of an incubated plating medium of the present invention, is an indication of the presence of a microorganism other than *Escherichia coli* 0157:H7. Colonies produced by a microorganism which is both a sorbitol fermenter and beta-galactosidase positive are of a third color (green in the examples) that is a blend of the first and second colors, and most *Escherichia coli* other than *Escherichia coli* 0157:H7 are included in this group.

Sorbitol is the main carbohydrate ingredient of the plating medium. Other carbohydrates which are not fermented by *Escherichia coli* 0157:H7 are salicin, inositol and adonitol, and these compositions and sorbitol, or a mixture thereof, have been found suitable for the carbohydrate ingredient of the plating media. Alternative carbohydrates at concentrations up to 10.0 grams per liter are mannitol, dulcitol, d-sorbitol, L-arabinose, L-rhamnose, d-xylose, trehalose, d-mannose and melibiose.

Indoxyl-beta-D-galactopyranoside is a chromogen which determines the presence of beta-galactosidase. Beta-galactosidase is an enzyme produced by *Escherichia coli* and other coliforms, and this enzyme reacts with indoxyl-beta-D-galactopyranoside to produce an insoluble indigo blue precipitate. Other chromogens may be used in place of, or in combination with, indoxyl-beta-D-galactopyranoside, such as 5-bromo-4-chloro-3-indoxyl-beta-D-galactopyranoside.

In the preferred embodiment, isopropyl-beta-D-thiogalactopyranoside is also added to the plating medium. This ingredient enhances the production of the beta-galactosidase enzyme.

In the preferred embodiment of the present invention, other inhibitors which will not inhibit the growth of *Escherichia coli* 0157:H7 are employed in addition to tellurite. An inhibitor for gram positive bacteria is also utilized, and in the preferred composition it is bile salts #3. Other inhibitors of gram positive bacteria can also be employed.

The medium of the preferred embodiment also contain a growth inhibitor for Proteus sp, namely, sodium novobiocin. Other inhibitors for Proteus sp. could also be employed.

The medium of the present invention also contain nutrients to promote the growth of microorganisms, especially protein. In the preferred embodiment, a mixture of tryptone, bacto-peptone and proteose-peptone is used, but it is to be understood that each of these ingredients can be separately used or used in combination with other nutrients. Further, there are many other nutrients which will support the growth of microorganisms which may be used in place of the above named nutrients.

The preferred embodiment also uses a pH indicator dye to permit ready determination of the pH of the medium. The pH of the medium should be adjusted to 6.6 to 6.8. Sodium chloride is also added to the medium for osmolarity purposes.

There are some strains of *Escherichia coli*, including *Escherichia coli* 0157:H7 and some other microorganisms, that are not sorbitol fermenters or beta-galactosidase positive, but are beta-glucuronidase active. The medium described above is not responsive to such microorganisms, but is more specific to *Escherichia coli* 0157:H7. Optionally, a beta-glucuronidase chromogen may be admixed with the medium to produce a response to beta-glucuronidase. A preferred beta-glucuronidase chromogen is 6-chloro-3-indoxyl-beta-D-glucuronide which responds to beta-glucuronidase by producing a salmon precipitate in the plating medium which may be observed and counted.

The preferred embodiment of a plating medium contains the ingredients in the proportions set forth in the following Table I.

TABLE I

| MATERIAL | MEASUREMENT |
| --- | --- |
| Tryptone | 5.0 grams/liter |
| Bacto-peptone | 10.0 grams/liter |
| Proteose-peptone | 3.0 grams/liter |
| Sorbitol | 12.0 grams/liter |
| Salicin | 10.0 grams/liter |
| Inositol | 10.0 grams/liter |
| Adonitol | 8.0 grams/liter |
| Sodium chloride | 5.0 grams/liter |
| Phenol red | 0.1 grams/liter |
| Bile salts #3 | 1.25 grams/liter |
| indoxyl-beta-D-galactopyranoside | 0.120 grams/liter |
| 5-bromo-4-chloro-3-indoxyl-beta-D-galactopyranoside | 0.120 grams/liter |
| isopropyl-beta-D-thiogalactopyranoside | 0.100 grams/liter |
| Agar | 15 grams/liter |
| Novobiocin | 10 milligrams per liter |
| Potassium tellurite | 0.5 to 2.0 milligrams/liter |
| OPTIONAL 6-chloro-3-indoxyl-beta-D-glucuronide | 0.120 grams/liter |

Except for novobiocin and potassium tellurite, the ingredients are mixed in any order, the pH adjusted to 6.6 to 6.8, boiled to sterilize the mixture, and the mixture is permitted to cool to room temperature. Thereafter sterile novobiocin and sterile potassium tellurite at room temperature are added aseptically to the other ingredients. The composition is then poured into plates and permitted to dry for 48 to 72 hours, and it is then ready to be used. Storage of poured plates is as much as 90 days at 2 to 8 degrees Celsius.

The process of the present invention requires a plate or mass of the plating medium to be inoculated with the test sample, and the inoculated mass is then incubated for a period of time to permit growth of the microorganisms in the test sample to observable colonies. The inventor has found that with the preferred plating medium described above, a period of 24 hours of incubation is sufficient time for *Escherichia coli* 0157:H7 colonies present in raw hamburger to grow into colonies which are readily observable with a naked eye. It is believed that the abundant growth of microorganisms in the preferred plating medium is due to the nutrients provided by the tryptone, bacto-peptone, proteose-peptone, sorbitol salicin, inositol and adonitol. The surface of the plating medium mass is then assayed and the presence and number of blue with black precipitate colonies recorded. Also, the presence of white or yellow to green colored colonies is noted as an indication of microorganisms other than *Escherichia coli* 0157:H7.

It is to be noted that no special equipment is required to observe the incubated mass of plating medium. The time required to note the number and presence of blue with black precipitate colonies is far less than required when other colonies are present. Also, there are no ingredients in the plating medium that are especially costly. Hence, an assay of a test sample may be made at reduced cost from assays with prior plating media.

The following Table II sets forth examples of use of the plating medium set forth in Table I, without the optional substrate, by the process described above, the test sample containing the microorganism shown in the left column and the observed colonial description being set forth in the right column.

TABLE II

| Bacterial species | # of Strains | Colonial Morphology |
| --- | --- | --- |
| *Escherichia coli* 0157:H7 Typical strains | 26 | Domed to raised colony; 1.5–2.5 mm in diameter. Dark blue to black color. No ring around colony. |
| *Escherichia coli* 0157:H7 Beta-glucuronidase positive | 1 | Domed to raised colony; 2.0 mm in diameter. Dark blue to black color. No ring around colony. |
| *Escherichia coli* 0157:H7 Sorbitol positive | 1 | Domed to raised colony; 2.0 mm in diameter. Blue to turquoise color. No ring around colony. |
| *Escherichia hermannii* | 2 | Domed; pinpoint to <1 mm in diameter; clear to light blue color |
| *Escherichia coli* | 9 | 3 strains no growth. Pinpoint to 2 mm in diameter; clear to green color. |
| Salmonella spp. | 5 | Minimal growth; <1 to 1 mm in diameter; clear/white to yellow color |
| *Pseudomonas cepacia* | 1 | Domed; 1 to 2 mm in diameter. Clear color. |
| *Pseudomonas aeruginosa* | 2 | Domed; pinpoint to <1 mm in diameter. Clear color. |
| *Providencia stuartii* | 1 | Domed; <1 mm in diameter. Clear to white color. |
| *Pseudomonas picketti* Klebsiella spp Enterobacter spp. Proteus spp. Morganella sp. Citrobacter spp. *Acinetobacter calcoaceticus* *Providencia alcalifaciens* *Yersinia enterocolitica* | 16 | No growth for all strains |

Those skilled in the art will devise other methods of utilizing the plating media of the present invention, and other plating media than those specifically described in the foregoing specification within the scope of the present invention. It is therefore intended that the scope of the present invention be not limited by the foregoing specification, but rather only by the appended claims.

The invention claimed is:

1. An isolation plating medium for use in processes for the presumptive identification of *Escherichia coli* O157:H7 consisting essentially of a mixture of (1) an ingredient which selectively promotes growth of *Escherichia coli* cells under incubation, (2) an ingredient that inhibits growth of gram positive microorganisms under incubation, (3) an ingredient that inhibits growth of Proteus sp. under incubation, (4) an ingredient that inhibits the growth of strains of *Escherichia coli* other than *Escherichia coli* O157:H7 under incubation, (5) a plurality of carbohydrates selected from the group consisting of sorbitol, salicin, inositol, and adonitol, (6) a pH indicator dye that changes the color of the plating medium to a first color when the pH of the medium changes, (7) a chromogenic substrate that reacts to beta-galactosidase to form a precipitate of a second color which contrasts with the first color, whereby a microorganism which ferments one or more of the carbohydrates but does not produce beta-galactosidase will produce colonies in the plating medium of the first color, a microorganism which does not ferment a carbohydrate but produces beta-galactosidase will produce colonies in the plating medium of the second color, and a microorganism which ferments at least one of the carbohydrates and produces beta-galactosidase will produce colonies in the medium of a third color which is a mixture of the first and second colors, and (8) a sufficient mass of an agent to solidify the mixture.

2. An isolation plating medium for use in processes for the presumptive detection of *Escherichia coli* O157:H7 consisting essentially of the mixture of claim 1 in combination with an ingredient which provides nutrients to facilitate the growth of microorganisms.

3. An isolation plating medium for use in processes for the presumptive detection of *Escherichia coli* O157:H7 consisting essentially of the mixture of claim 2 wherein the ingredient which provides nutrients to facilitate the growth of microorganisms comprises one or more members of the group tryptone, bacto-peptone, and proteose-peptone.

4. An isolation plating medium for use in processes for the presumptive detection of *Escherichia coli* O157:H7 consisting essentially of the mixture of claim 1 in combination with isopropyl-beta-D-thiogalactopyranoside.

5. An isolation plating medium for use in processes for the presumptive detection of *Escherichia coli* O157:H7 consisting essentially of the mixture of claim 1 wherein the chromogenic beta galactosidase substrate which forms a second color upon reacting to beta-galactosidase comprises a member selected from the group consisting of indoxyl-beta-D-galactopyranoside and 5-bromo-4-chloro-3-indoxyl-beta-D-galactopyranoside.

6. An isolation plating medium for use in processes for the presumptive detection of *Escherichia coli* O157:H7 consisting essentially of the mixture of claim 1 wherein the ingredient which inhibits the growth of Proteus sp. consists essentially of sodium novobiocin.

7. An isolation plating medium for use in processes for the presumptive detection of *Escherichia coli* O157:H7 consisting essentially of the mixture of claim 1 wherein the ingredient which inhibits the growth of *Escherichia coli* strains other than *Escherichia coli* O157:H7 consists essentially of potassium tellurite.

8. An isolation plating medium for use in processes for the presumptive detection of *Escherichia coli* O157:117 consists essentially of a mixture of (1) an ingredient that selectively promotes the growth of *Escherichia coli* cells under incubation consisting essentially of one or more members of the group tryptone, bacto-peptone, and proteose-peptone, (2) an ingredient that inhibits the growth of gram positive microorganisms consisting essentially of bile salts, (3) an ingredient that inhibits the growth of Proteus sp. consisting essentially of sodium novobiocin, (4) an ingredient that inhibits the growth of strains of *Escherichia coli* other than *Escherichia coli* O157:H7 consisting essentially of potassium tellurite, (5) a carbohydrate medium consisting essentially of a plurality of the members of the group sorbitol, salicin, inositol, and adonitol, said carbohydrate medium forming colonies responsive to microorganisms which ferment the medium, (6) a pH indicator dye which changes the color of the carbohydrate medium to a first color when the pH of the medium changes consisting essentially of phenol red, the mixture having a pH of 6.6 to 6.8 before being exposed to a test sample, (7) a chromogenic beta-galactosidase substrate which forms a second color upon reacting to beta-galactosidase consisting essentially of one or more members of the group indoxyl-beta-D-galactopyranoside and 5-bromo4-chloro-3-indoxyl-beta-D-galactopyranoside, and (8) a mass of agar sufficient to solidify the mixture, whereby a microorganism that ferments one or more of the carbohydrates but does not produce beta-galactosidase will produce colonies in the plating medium of the first color, a microorganism which does not ferment a carbohydrate but produces beta-galactosidase will produce colonies in the plating medium of the second color, and a microorganism which ferments at least one of the carbohydrates and produces beta-galactosidase will produce colonies in the medium of a third color which is a mixture of the first two colors.

9. An isolation plating medium for use in processes for the presumptive detection of *Escherichia coli* O157:H7 consisting essentially of the mixture of claim 8 and a mass of sodium chloride admixed therein.

10. An isolation plating medium for use in processes for the presumptive detection of *Escherichia coli* O157:H7 comprising (1) an ingredient that promotes the growth of *Escherichia coli* cells under incubation consisting essentially of one or more members of the group tryptone, bacto-peptone, and proteose-peptone, (2) an ingredient that inhibits the growth of gram positive microorganisms consisting essentially of bile salts, (3) an ingredient that inhibits the growth of Proteus sp. consisting essentially of sodium novobiocin, (4) an ingredient that inhibits the growth of strains of *Escherichia coli* other than *Escherichia coli* O157:H7 consisting essentially of potassium tellurite, (5) a carbohydrate medium consisting essentially of a plurality of the members of the group sorbitol salicin, inositol, and adonitol, said carbohydrate medium forming colonies responsive to microorganisms upon incubation, (6) a pH indicator dye which changes the color of the carbohydrate medium to a first color when the pH of the medium changes consisting essentially of phenol red, the media having a pH of 6.6 to 6.8 before being exposed to a test sample, (7) a chromogenic beta-galactosidase substrate which produces a precipitate of a second color upon reacting to beta-galactosidase consisting essentially of one or more members of the group indoxyl-beta-D-galactopyranoside and 5-bromo-4-chloro-3-indoxyl-beta-D-galactopyranoside, (8) a mass of agar sufficient to solidify the mixture, and (9) a mass of 6-chloro-3-indoxyl-beta-D-glucuronide mixed therein, whereby a microorganism that ferments one or more of the carbohydrates but does not produce beta-galactosidase will produce colonies in the plating medium of the first color, a microorganism which does not ferment a carbohydrate but produces beta-galactosidase will produce colonies in the plating medium of the second color, and a microorganism which ferments at least one of the carbohydrates and produces beta-galactosidase will produce colonies in the medium of a third color which is a mixture of the first two colors.

11. An isolation plating medium for use in processes for the presumptive detection of *Escherichia coli* 0157:H7 comprising a mixture of 5.0 grams per liter tryptone, 10.0 grams per liter bacto-peptone, 3.0 grams per liter proteose-peptone, 1.25 grams per liter bile salts #3, 10 milligrams per liter of sodium novobiocin, 0.5 to 2.0 milligrams per liter potassium tellurite, 12.0 grams per liter sorbitol, 10.0 grams per liter salicin, 10.0 grams per liter inositol, 15.0 grams per liter agar, 8.0 grams per liter adonitol, 120 milligrams per liter indoxyl-beta-D-galactopyranoside, 120 milligrams per liter 5-bromo-4-chloro-3-indoxyl-beta-D-galactopyranoside, 100 milligrams per liter isopropyl-beta-D-thiogalactopyranoside, 0.100 gram per liter phenol red, and 5.0 grams per liter sodium chloride, the mixture having a pH of 6.6 to 6.8 before being exposed to a test sample.

12. An isolation plating medium for use in processes for the presumptive detection of *Escherichia coli* 0157:H7 comprising the mixture of claim 11 including 120 milligrams per liter 6-chloro-3-indoxyl-beta-D-glucuronide.

13. The method of detecting the presence of *Escherichia coli* 0157:H7 in a test sample comprising the steps of inoculating a solid plating medium with said test sample, wherein said plating medium consists essentially of a mixture of (1) an ingredient which promotes growth of *Escherichia coli* cells, (2) an ingredient which inhibits growth of gram positive microorganisms, (3) an ingredient which inhibits growth of Proteus sp., (4) an ingredient which inhibits growth of strains of *Escherichia coli* other than *Escherichia coli* 0157:H7, (5) a carbohydrate medium containing a plurality of carbohydrates selected from the group consisting of sorbitol, salicin, inositol, and adonitol, said carbohydrate medium producing colonies upon fermentation, (6) a pH indicator dye which changes the color of the plating media to a first color when the pH of the medium changes, (7) a chromogenic beta-galactosidase substrate which reacts to beta-galactosidase to form precipitate of a second color which contrasts with the first color, whereby a microorganism which ferments the carbohydrate medium but does not produce beta-galactosidase will produce colonies in the medium of the first color, a microorganism which does not ferment the carbohydrate medium but produces beta-galactosidase will produce colonies in the medium of the second color, and a microorganism which ferments the carbohydrate medium and produces beta-galactosidase will produce colonies in the medium of a third color which is a mixture of the first and second colors and (8) a mass of agar sufficient to solidify the mixture, thereafter incubating said plating medium for a sufficient period to obtain colonies of microorganisms producing one or more of said colors, and examining the surface of said plating medium for colonies of said first, second and third colors.

14. The method of detecting the presence of *Escherichia coli* 0157:H7 in a test sample comprising the steps of inoculating a solid plating medium with said test sample, wherein said plating medium comprises a mixture of 5.0 grams per liter tryptone, 10.0 grams per liter bacto-peptone, 3.0 grams per liter proteose-peptone, 1.25 grams per liter bile salts #3, 10 milligrams per liter of sodium novobiocin, 0.5 to 2.0 milligrams per liter potassium tellurite, 12.0 grams per liter sorbitol, 10.0 grams per liter salicin, 10.0 grams per liter inositol, 8.0 grams per liter adonitol, 120 milligrams per liter indoxyl-beta-D-galactopyranoside, 120 milligrams per liter 5-bromo-4-chloro-3-indoxyl-beta-D-galactopyranoside, 100 milligrams per liter isopropyl-beta-D-thiogalactopyranoside, 0.10 grams per liter phenol red, 5.0 grams per liter sodium chloride, and 15 grams per liter of agar, the mixture having a pH of 6.6 to 6.8 before being exposed to a test sample, then incubating said plating medium for at least 24 hours to obtain colonies of microorganisms generating one or more of said colors, and then examining the surface of said plating medium for colonies of colors differing from the color of the remainder of the plating media.

15. An isolation plating medium for use in processes for the presumptive detection of *Escherichia coli* 0157:H7 consisting essentially of a mixture of a carbohydrate medium containing a plurality of carbohydrates selected from the group sorbitol, salicin, inositol, and adonitol, a pH indicator dye which changes the color of the medium to a first color when the pH of the medium changes consisting essentially of phenol red, the mixture having a pH of 6.6 to 6.8 before being exposed to a test sample, a chromogenic beta-galactosidase substrate which forms precipitate of a second color upon reacting to beta galactosidase consisting essentially of one or more members of the group indoxyl-beta-D-galactopyranoside and 5-bromo-4-chloro-3-indoxyl-beta-D-galactopyranoside, and a mass of agar sufficient to solidify the mixture, whereby a microorganism which ferments the carbohydrate medium but does not produce beta-galactosidase will produce colonies in the medium of the first color, a microorganism which does not ferment the carbohydrate medium but produces beta-galactosidase will produce colonies in the medium of the second color, and a microorganism which ferments the carbohydrate medium and produces beta-galactosidase will produce colonies in the medium of a third color which is a mixture of the first and second colors.

16. An isolation plating medium for use in processes for the presumptive detection of *Escherichia coli* 0157:H7 consisting essentially of the mixture of claim 15 and an ingredient that promotes the growth of *Escherichia coli* cells under incubation using one or more members of the group tryptone, bacto-peptone, and proteose-peptone.

17. An isolation plating medium for use in processes for the presumptive detection of *Escherichia coli* 0157:H7 consisting essentially of the media of claim 15 wherein the carbohydrate medium consists of a plurality of the members of the group sorbitol, salicin, inositol and adonitol.

18. An isolation plating medium for use in processes for the presumptive identification of *Escherichia coli* 0157:H7 comprising a mixture of an ingredient which selectively promotes growth of *Escherichia coli* cells under incubation, a plurality of carbohydrates selected from the group consisting of sorbitol, salicin, inositol, and adonitol, fermentation of said carbohydrates by a microorganism forming colonies in the plating medium, a pH indicator dye that changes the color of the plating medium to a first color when the pH of the medium changes, a chromogenic substrate that reacts to beta-galactosidase to form a precipitate in the plating medium of a second color which contrasts with the first color, whereby a microorganism which ferments one or more of the carbohydrates but does not produce beta-galactosidase will produce colonies in the plating medium of the first color, a microorganism which does not ferment the carbohydrate medium but produces beta-galactosidase will produce colonies in the plating medium of the second color, and a microorganism which ferments the carbohydrate medium and produces beta-galactosidase will produce colonies in the plating medium of a third color which is a mixture of the first and second colors, and a sufficient mass of an agent to solidify the mixture.

19. The method of detecting the presence of one bacterial strain in a test sample containing other bacterial strains comprising the steps of inoculating a solid plating medium with said test sample, wherein said plating medium comprises a mixture of an ingredient which selectively promotes growth of the one bacterial strain, said one bacterial strain releasing an enzyme into the medium upon catabolization of the growth promoting ingredient, a carbohydrate medium containing a plurality of different carbohydrates selected from the group consisting of sorbitol, salicin, inositol, and adonitol, and producing colonies in the plating medium upon fermentation, a pH indicator dye that changes the color of the plating medium to a first color when the pH of the medium changes, a chromogenic substrate which reacts to the enzyme released by the one bacterial strain upon catabolization of the growth ingredient to form precipitate of a second color which contrasts with the first color, whereby a bacterial strain that ferments the carbohydrate medium but does not produce the enzyme of the one bacterial strain will produce colonies in the medium of the first color, a bacterial strain that does not ferment the carbohydrate medium but produces the enzyme released by the one bacterial strain will produce colonies in the medium of the second color, and a bacterial strain that ferments the carbohydrate medium and produces the enzyme of the one bacterial strain will produce colonies in the medium of a third color which is a mixture of the first and second colors, and a mass of an agent sufficient to solidify the mixture, thereafter incubating said plating medium for a sufficient period to obtain colonies of bacterial strains producing one or more of said colors, and examining the plating medium for colonies of said first second and third colors.

* * * * *